US012523139B2

(12) United States Patent
Jones et al.

(10) Patent No.: US 12,523,139 B2
(45) Date of Patent: Jan. 13, 2026

(54) PROXY FLUID TO DETERMINE EFFECTIVENESS OF A COATING FOR WELLBORE EQUIPMENT

(71) Applicant: Halliburton Energy Services, Inc., Houston, TX (US)

(72) Inventors: Christopher Michael Jones, Houston, TX (US); James Martin Price, Houston, TX (US); Darren George Gascooke, Houston, TX (US); Anthony Herman Vanzuilekom, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 454 days.

(21) Appl. No.: 18/298,531

(22) Filed: Apr. 11, 2023

(65) Prior Publication Data

US 2024/0344444 A1 Oct. 17, 2024

(51) Int. Cl.
*E21B 47/005* (2012.01)
*E21B 49/08* (2006.01)
*G01N 17/00* (2006.01)
*G01N 33/26* (2006.01)

(52) U.S. Cl.
CPC ........ *E21B 47/005* (2020.05); *E21B 49/0875* (2020.05); *G01N 17/00* (2013.01); *G01N 33/26* (2013.01)

(58) Field of Classification Search
None
See application file for complete search history.

(56) References Cited

U.S. PATENT DOCUMENTS

2007/0062695 A1* 3/2007 Harrison ................. E21B 49/10 166/250.11
2011/0277995 A1 11/2011 Wilkinson et al.
2014/0338900 A1* 11/2014 Jones ...................... E21B 49/10 166/264
2017/0227450 A1 8/2017 Hoegerl et al.
2018/0024044 A1 1/2018 Ringgenberg et al.
2018/0252679 A1 9/2018 Bonadies, Jr. et al.

FOREIGN PATENT DOCUMENTS

WO 2020032795 A1 2/2020

* cited by examiner

*Primary Examiner* — Daniel S Larkin
(74) *Attorney, Agent, or Firm* — Sheri Higgins Law, PLLC; Sheri Higgins

(57) ABSTRACT

Wellbore equipment used in oil and gas operations can be negatively affected by corrosive fluids. Coatings can be applied to the equipment to help protect the equipment. A field test can be used at a wellsite to ensure the coating is effective. Due to the HSE risks of the corrosive fluids, a proxy fluid can be used instead. The proxy fluid can have similar chemical or physical properties and simulate the corrosive fluid that is anticipated to be present in the wellbore. The wellbore equipment that is coated can be sealed to create a containment area where an initial concentration of the proxy fluid is introduced into the containment area for a period of time. A final concentration of the proxy fluid can be measured after the period of time has elapsed. By calculating the percent change of the proxy fluid, the effectiveness of the coating can be determined.

20 Claims, 2 Drawing Sheets

PROXY FLUID TO DETERMINE EFFECTIVENESS OF A COATING FOR WELLBORE EQUIPMENT

TECHNICAL FIELD

A variety of downhole tools are used in oil and gas operations. A coating can be applied to the tools to protect components of the tools against corrosive fluids or against absorption of fluids into tool component materials. A proxy fluid can be used to determine the effectiveness of the coating.

BRIEF DESCRIPTION OF THE FIGURES

The features and advantages of certain embodiments will be more readily appreciated when considered in conjunction with the accompanying figures. The figures are not to be construed as limiting any of the preferred embodiments.

DETAILED DESCRIPTION

Figure 1:
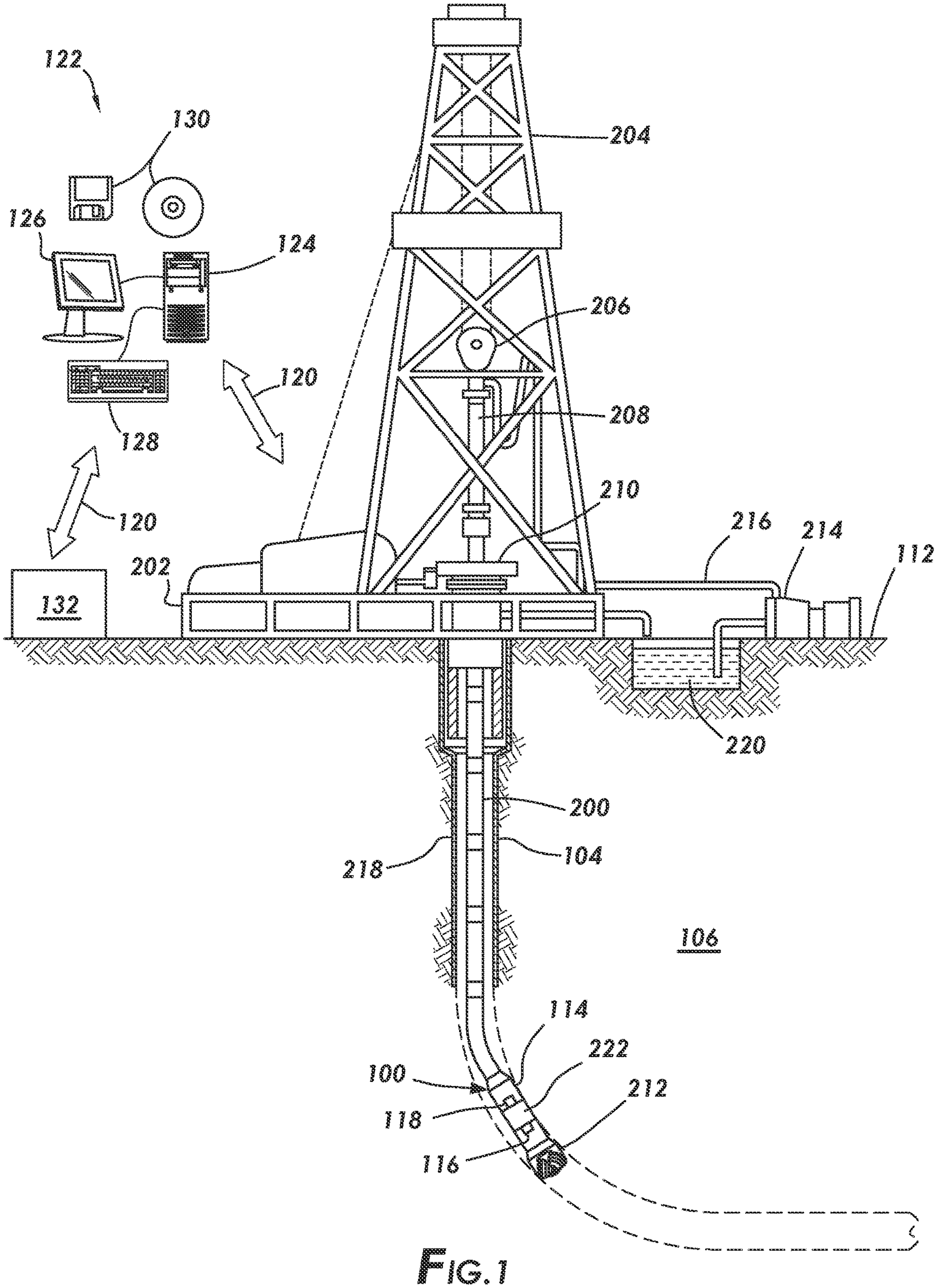
FIG. 1 is a schematic diagram of an example of a formation testing tool on a drill string according to certain embodiments.

Oil and gas hydrocarbons are naturally occurring in some subterranean formations. In the oil and gas industry, a subterranean formation containing oil and/or gas is referred to as a reservoir. A reservoir can be located under land or offshore. Reservoirs are typically located in the range of a few hundred feet (shallow reservoirs) to a few tens of thousands of feet (ultra-deep reservoirs). In order to produce oil or gas, a wellbore is drilled into a reservoir or adjacent to a reservoir. The oil, gas, or water produced from a reservoir is called a "reservoir fluid." As used herein, a "fluid" is a substance having a continuous phase that can flow and conform to the outline of its container when the substance is tested at a temperature of 71° F. (22° C.) and a pressure of one atmosphere "atm" (0.1 megapascals "MPa"). A fluid can be a liquid or gas.

A well can include, without limitation, an oil, gas, or water production well, an injection well, or a geothermal well. As used herein, a "well" includes at least one wellbore. A wellbore can include vertical, inclined, and horizontal portions, and it can be straight, curved, or branched. As used herein, the term "wellbore" includes any cased, and any uncased, open-hole portion of the wellbore. A near-wellbore region is the subterranean material and rock of the subterranean formation surrounding the wellbore. As used herein, a "well" also includes the near-wellbore region. The near-wellbore region is generally considered to be the region within approximately 100 feet radially of the wellbore. As used herein, "into a subterranean formation" means and includes into any portion of the well, including into the wellbore, into the near-wellbore region via the wellbore, or into the subterranean formation via the wellbore.

There are a variety of tools used in oil and gas operations. One such tool is a downhole formation tester tool. The formation tester tool typically includes a combination of different in-situ sensors for real time fluid identification, as well as PVT sampling chambers that allow a captured fluid to be transported to the surface or lab for more in-depth analysis. The tool can be used to collect samples of a reservoir fluid. The samples can then be sent to a laboratory where analysis of the reservoir fluid, such as gas chromatography, can be used to determine the chemical makeup of components in the reservoir fluid. Another example of a tool is a measurement while drilling (MWD) tool. A MWD is a well logging tool that incorporates a measurement tool into a drilling string to provide real-time information during a drilling operation, such as helping to steer the drilling string or interrogate one or more formation properties.

Some reservoir fluids can contain corrosive and/or dangerous components. Corrosive fluids can corrode various components of downhole tools and tubing strings. As used herein, the term "corrosive fluid" means a fluid that can cause corrosion, degrade via etching or eating away, or erode a material such as a metal or metal alloy. For example, some microorganisms present in wellbore fluids can produce hydrogen sulfide ($H_2S$) gas as a respiration end product, which accumulates extracellularly during consumption. It is undesirable for a well to contain high amounts of a sour gas, such as hydrogen sulfide gas. A well containing greater than 5 parts per million (ppm) of a sour gas is commonly called a sour gas well, while a well containing less than 5 ppm of a sour gas is commonly called a sweet well. Sour gas is considered to be a corrosive substance, which can be detrimental to wellbore operations; for example, harmful to wellbore equipment, such as downhole tools or tubing strings. Hydrogen sulfide is a very poisonous, corrosive, and flammable compound requiring serious health, safety, and environmental considerations under any operational environment where it may exist (even in trace amounts). If present in a reservoir, additional mitigating processes and capital investment are needed at every stage of the lifecycle of the well to protect the health and safety of personnel and protect the environment.

Moreover, some oil or gas treatment fluids can include corrosive ingredients, for example an acid. However, acid treatments can create additional risks-especially in high temperature wells due to corrosivity issues and generation of toxic hydrogen sulfide gas during application. Another example of a corrosive and/or dangerous component is mercury (Hg). Mercury is a natural occurring element and can be present in various stages of oil and gas operations. Mercury is not only hazardous to human health, safety, and the environment but can also attack downhole tool components or equipment that include mercury-reactive materials.

Some reactive materials making up downhole tool components can absorb a corrosive fluid. Chemical absorption or reactive absorption is a chemical reaction between the absorbed and the absorbing material. Chemical or reactive absorption can also combine with physical absorption and can be dependent upon the stoichiometry of the reaction and the concentration of its reactants. Accordingly, damage or impairment of the downhole tool can occur, which can be costly to repair or replace the tool and result in downtime where the oil or gas operation must halt.

Therefore, a coating can be applied to oil and gas equipment, such as downhole tools or tubing strings, to protect against these corrosive and dangerous fluids. The coating can be made from an inert material that does not react with, adhere with, or otherwise consume the corrosive fluids. Moreover, accurate reservoir fluid identification and sampling of hydrogen sulfide contaminated fluids can be difficult to achieve due its consumption by the interior of downhole tool surfaces prior to sampling or measurement. Consequently, $H_2S$ concentrations are typically under-reported, which adversely affects production and presents significant health safety and environment concerns. Because it is critical to obtain accurate information regarding the $H_2S$ content as early as possible during the exploration phase in order to plan and develop the appropriate health, safety, and environmental protocols, flow assurance, and production strategies, reservoir sampling tools can also be coated to provide accurate concentrations of $H_2S$.

The coatings can be a very thin layer, oftentimes one micrometer or less. Therefore, it may be impossible to visually inspect the coated areas to ensure that the coating is uniform and placed in every area that the coating is needed. Measuring the thickness of the coating can help to ensure that the coating has been properly applied but does not prove that the equipment is protected against absorption of the corrosive fluids. Moreover, coatings can become cracked or damaged after application of the coating and prior to use, for example during transport of the equipment to the wellsite, thus decreasing the effectiveness of the coating. Thus, there is a need to be able to ensure that the coating is effective to provide the desired protection against absorption of the corrosive fluids.

Due to the health, safety, and environmental (HSE) risks, the corrosive fluid itself may not be used to test the effectiveness of the coating. Thus, there is a need for a test that can determine the effectiveness of a coating that does not pose HSE risks. It has been discovered that a test can be performed using a proxy fluid that is safe and does not pose HSE risks.

A system can include a wellbore equipment; a coating applied to a portion of the wellbore equipment; an initial concentration of a proxy fluid contained for a period of time within the wellbore equipment adjacent to the coating; and a measuring device that determines a final concentration of the proxy fluid after the period of time has elapsed.

A method for testing an effectiveness of a coating applied to wellbore equipment can include creating a containment area within the wellbore equipment containing the coating; placing an initial concentration of a proxy fluid within the containment area; allowing the proxy fluid to remain within the containment area for a period of time; and measuring a final concentration of the proxy fluid after the period of time has elapsed.

The various disclosed embodiments can apply to the systems and method embodiments without the need to repeat the various embodiments throughout for each of the systems and methods.

A coating can be applied to a portion of wellbore equipment. The wellbore equipment can be any equipment that is placed downhole into a subterranean formation and used in oil and gas operations. The wellbore equipment may be exposed to and come in contact with corrosive fluids in the subterranean formation. Non-limiting examples of wellbore equipment that can be coated include a downhole formation tester tool, a measurement while drilling (MWD) tool, or the inside or outside of a casing string or tubing string. The wellbore equipment can include a variety of components. Some or all of the components can be made from a material that is reactive to the corrosive fluid. Non-limiting examples of materials that are reactive include steel, titanium, Inconel, and MP35N, which is a superalloy containing primary elements of cobalt, nickel, chromium, and molybdenum. The coating can be made from a material that is non-reactive to the corrosive fluids. All of the components or just some of the components can be coated. By way of example, if some of the components are made from a material that is non-reactive to contact with the corrosive fluids, then those components may not need to be coated.

The coating can be applied to the wellbore equipment by any method. The coating can be applied to the wellbore equipment prior to use in an oil and gas operation, for example, offsite or onsite in the field. The corrosive fluids that may contact the wellbore equipment include but are not limited to hydrogen sulfide gas, mercury, and acids such as hydrochloric acid (HCl).

After the coating has been applied, a field test can be performed to determine if the coating is effective at preventing or substantially reducing the amount of the corrosive fluid that is absorbed into reactive materials of the wellbore equipment, which could cause damage to the wellbore equipment. The field test is preferably performed in the field at the wellsite where the coated wellbore equipment is to be used. As discussed above, due to the health, safety, and environmental risks associated with the corrosive fluids, it is not preferable to perform the test with the corrosive fluids. Accordingly, a proxy fluid can be used to perform the test. As used herein, a "proxy fluid" is any fluid in a liquid or gas form that has similar chemical or physical properties to that of the corrosive fluid. By way of example, if the corrosive fluid is $H_2S$, then the proxy fluid has similar chemical or physical properties to that of $H_2S$. In this manner, the proxy fluid can simulate the corrosive fluid. According to any of the embodiments, the proxy fluid does not pose health, safety, or environmental risks.

The similar chemical or physical properties include but are not limited to molecular weight, vapor pressure, boiling point, electronegativity, ionizable protons, pKa, and temperature desorption characteristics (TPD). The proxy fluid can have one or more than one chemical or physical property that is similar to the corrosive fluid. A proxy fluid having more than one similar chemical or physical property may be beneficial to better simulate the corrosive fluid.

The proxy fluid can be, for example, water vapor, nitrous acid ($HNO_2$), sulfur dioxide ($SO_2$), phosphoric acid ($H_3PO_4$), acetic acid ($CH_3COOH$), phenolic acid, or sulfoxylic acid ($H_2SO_2$). The proxy fluid can have similar chemical or physical properties to more than one corrosive fluid. By way of example, the proxy fluid can simulate both $H_2S$ and an acid or simulate both $H_2S$ and mercury.

The coated portion of the wellbore equipment to be tested can be closed off to create a containment area. An initial concentration of the proxy fluid can be introduced into the containment area. The manner in which the coated portion is closed off can be selected such that the proxy fluid can be introduced into the containment area. By way of example, a one-way valve can be located at an entry opening and another one-way valve can be located at an exit opening of the containment area. Any other openings into the containment area can be sealed off. By way of another example, a two-way valve can be located at one opening and any other openings can be sealed off. In this manner, the valves can be in a closed position prior to introduction of the proxy fluid. Then, the proxy fluid can be introduced within the containment area via the one-way valve located at the entry opening or via the two-way valve.

The initial concentration of the proxy fluid can be selected to be the same as or similar to the anticipated concentration of the corrosive fluid that may contact the wellbore equipment. The initial concentration can also be selected such that an accurate test can be performed. By way of example, if the initial concentration is too low, then accurate results may be difficult to achieve. The initial concentration can be in the range of 50 to 500 parts per million (ppm) for example.

The proxy fluid is contained within the containment area for a period of time. The period of time can range from 1 hour to 100 hours. The period of time can be selected based on industry standards, personnel, or the chemical reactivity rates and constants of the corrosive fluid and reactive material. The proxy fluid can be held within the containment area at a testing temperature, a pressure, or both. The testing temperature and pressure can be selected to simulate downhole conditions where the wellbore equipment is to be placed. The testing temperature can also be selected to decrease the period of time the proxy fluid is contained within the containment area. By way of example, increasing the testing temperature, for example above 73° F. (22.8° C.), can decrease the period of time (e.g., from 12 hours to 1 hour). The period of time and the testing temperature and pressure can be selected based on absorption rates and any temperature/pressure dependency of the corrosive fluid. By way of example, if $H_2S$ is the corrosive fluid expected to be encountered in the subterranean formation, then a test can be performed in a laboratory using $H_2S$. The laboratory can provide a safe environment in which to test with the corrosive fluid. An uncoated sample of the material to be coated, for example steel, can be contacted with the corrosive fluid. The absorption rate can then be determined, and any temperature/pressure dependency can also be determined. In this manner, the testing conditions in the field at the wellsite using the proxy fluid can be selected based on the laboratory test.

A measuring device can be used to measure a final concentration of the proxy fluid after the period of time has elapsed. The measuring device can be, for example, a mass spectrometer, an optical absorption spectrometer, a chemical sensor (e.g., an oxygen sensor), or quartz crystal microbalance sensor. The proxy fluid can be released from the containment area and allowed to interact with the measuring device such that the concentration of the proxy gas can be measured. By way of example, the proxy fluid can be released from the containment area via the one-way valve located at the exit opening or via the two-way valve. The measuring device can measure the proxy gas directly as the proxy gas is being released from the containment area.

The percent change (shown below in Eq. 1) of the proxy fluid can be used to determine if the coating is effective to protect the wellbore equipment from the corrosive fluid. If the percent change is a negative number, this indicates a decrease in the concentration of the proxy fluid, for example because some of the proxy fluid was absorbed into the material through the coating or because not all the areas of the wellbore equipment were coated. A percent change equal to 100% means that none of the proxy fluid was absorbed into the material and represents a highly effective coating. There can also be some acceptable percent change that is less than 100%, which would indicate that some of the proxy fluid was absorbed. As used herein, the term "acceptable percent change" means the percent change that is greater than or equal to a percentage that would cause damage to the wellbore equipment or impede or impair an accurate analysis of component concentrations of a subterranean fluid. The acceptable percent change can differ depending in part on the specifics of the subterranean formation, the type of wellbore equipment that is coated, the type of corrosive fluid, or the specific oil and gas operation to be performed using the wellbore equipment. By way of example, if the percent change that would cause damage to the wellbore equipment or impede or impair an accurate analysis of formation fluids is determined to be 65%, then the acceptable percent change can be greater than or equal to 65%. In this manner, damage is substantially reduced or prevented. The acceptable percent change can be, for example, in a range of 75% to 100%.

$$\% \text{ Change} = \frac{\text{Final } Conc. - \text{Initial } Conc.}{\text{Final } Conc.} \times 100 \qquad \text{Eq. 1}$$

The proxy fluid may not absorb onto the reactive material of the wellbore equipment in a direct 1:1 ratio as the corrosive fluid does. Accordingly, the acceptable percent change may be different for the proxy fluid compared to the corrosive fluid. An absorbance correlation between the corrosive fluid and the proxy fluid can be determined. The absorbance correlation can be determined prior to performing the field test at the wellsite. This testing can be performed in a laboratory offsite. A sample wellbore component-either with or without the coating—can be tested first with the corrosive fluid using the systems and methods described herein. The percent change of the corrosive fluid can then be calculated. Another test can then be performed using the proxy fluid and the percent change calculated to determine the absorbance ratio or correlation between the two fluids. By way of example, if a coated sample wellbore component is first tested using mercury and the percent change is 100%, and then the coated sample wellbore component is tested using water vapor as the proxy fluid and the percent change is 80% (indicating 20% of the water vapor was lost due to absorption, then the absorbance correlation would be 1:0.8. This absorbance correlation can then be used in the field at the wellsite to test the specific coated wellbore equipment to be used in the oil and gas operation. Accordingly, if the results of the field test using water vapor provide a percent change of 80%, then that translates into a 100% percent change (no absorption) against mercury, which indicates a completely effective coating has been applied to the wellbore equipment. According to this example, if the acceptable percent change for mercury as the corrosive fluid is 80% to 100%, then the acceptable percent change results in the field when using water vapor as the proxy fluid would be 64% to 80%.

The proxy fluid selected may not have similar chemical or physical properties to all types of corrosive fluids expected to be encountered in the subterranean formation. For example, water vapor may have similar chemical or physical properties to $H_2S$ but not to mercury. Accordingly, more than one field test can be performed to determine the effectiveness of the coating using two different proxy fluids. A first field test can be performed according to the systems and methods described herein using a first proxy fluid that simulates a first corrosive fluid. A second field test can then be performed using a second proxy fluid that is different from the first proxy fluid that simulates a second corrosive fluid that is different from the first corrosive fluid. In this manner, the effectiveness of the coating can be determined for all corrosive fluids that may come in contact with the wellbore equipment in the subterranean formation.

Verification as to the effectiveness of the coating after being used in the oil or gas operation can be beneficial. For example, it may be beneficial to ensure that a coating on a downhole formation tester tool has not degraded during use in a formation. A verification test can be performed in the field after the wellbore equipment has been used downhole. By way of example, if the initial field test of a downhole formation tester tool had a percent change of 100% for a proxy fluid simulating $H_2S$, this would indicate that any concentration of $H_2S$ in the reservoir fluid should be completely accurate. Therefore, to ensure the accuracy of the $H_2S$ concentration, the downhole formation tester tool can be returned to the surface and the downhole formation tester tool can be re-tested using the same proxy fluid. If the results of the re-test are a percent change of 100%, then this can be used to verify the concentration of $H_2S$ in the reservoir fluid sample were indeed accurate. If the re-test results do not match the results from the initial field test, this can indicate the actual concentration of $H_2S$ in the reservoir fluid is underreported, in which case the actual concentration of $H_2S$ in the reservoir fluid can be extrapolated by comparing the percent change of the initial test with the re-test.

FIG. 1 is a schematic diagram showing but one example of a downhole tool that can be tested. The downhole tool can be a formation testing tool 100 disposed on a drill string 200 in a drilling operation. Formation testing tool 100 may be used to obtain a fluid sample of a reservoir fluid from subterranean formation 106. The reservoir fluid may be contaminated with well fluid (e.g., drilling fluid) from wellbore 104. As illustrated, a drilling platform 202 may support a derrick 204 having a traveling block 206 for raising and lowering drill string 200. A kelly 208 may support drill string 200 as it may be lowered through a rotary table 210. A drill bit 212 may be attached to the distal end of drill string 200 and may be driven either by a downhole motor and/or via rotation of drill string 200 from the surface 112. A pump 214 may circulate drilling fluid through a feed pipe 216 to kelly 208, downhole through interior of drill string 200, through orifices in drill bit 212, back to surface 112 via annulus 218 surrounding drill string 200, and into a retention pit 220.

Drill bit 212 may be just one piece of a downhole assembly that may include one or more drill collars 222 and formation testing tool 100. One or more of the drill collars 222 may form a tool body 114. Formation testing tool 100 may further include one or more sensors 116 for measuring properties of the fluid sample reservoir fluid, wellbore 104, subterranean formation 106, or the like. Formation testing tool 100 may obtain and separately store different fluid samples from subterranean formation 106 with fluid analysis module 118. Information from formation testing tool 100 may be transmitted to an information handling system 122, which may be located at surface 112. As illustrated, communication link 120 may be provided that may transmit data from formation testing tool 100 to an information handling system at surface 112. Information handling system may include a processing unit 124, a monitor 126, an input device 128, and/or computer media 130. A gas chromatographer 132 may be disposed on surface 112 and analyze samples captures by downhole fluid sampling tool 100.

Figure 2:
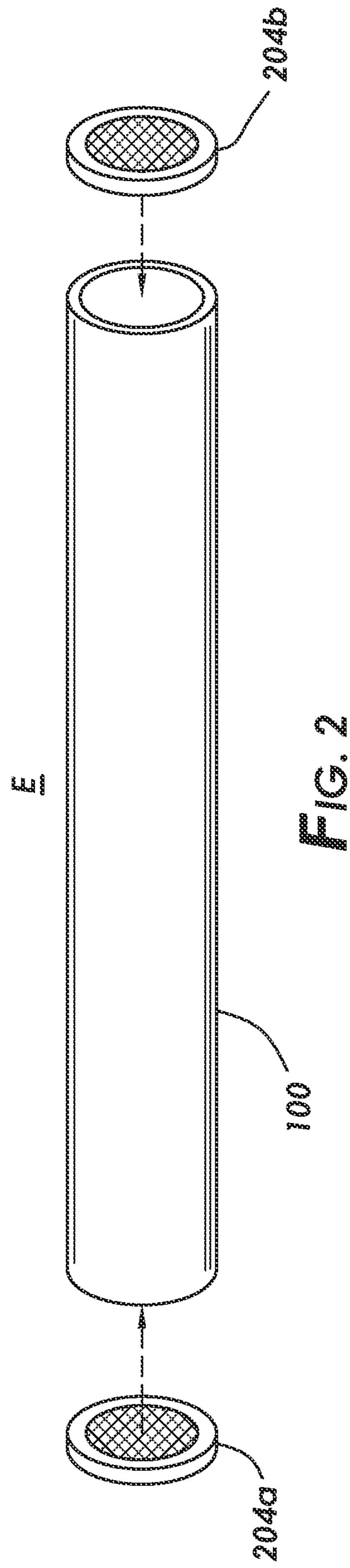
FIG. 2 is a perspective view of a portion of the formation testing tool and closures for creating a containment area according to certain embodiments.
Figure 3:
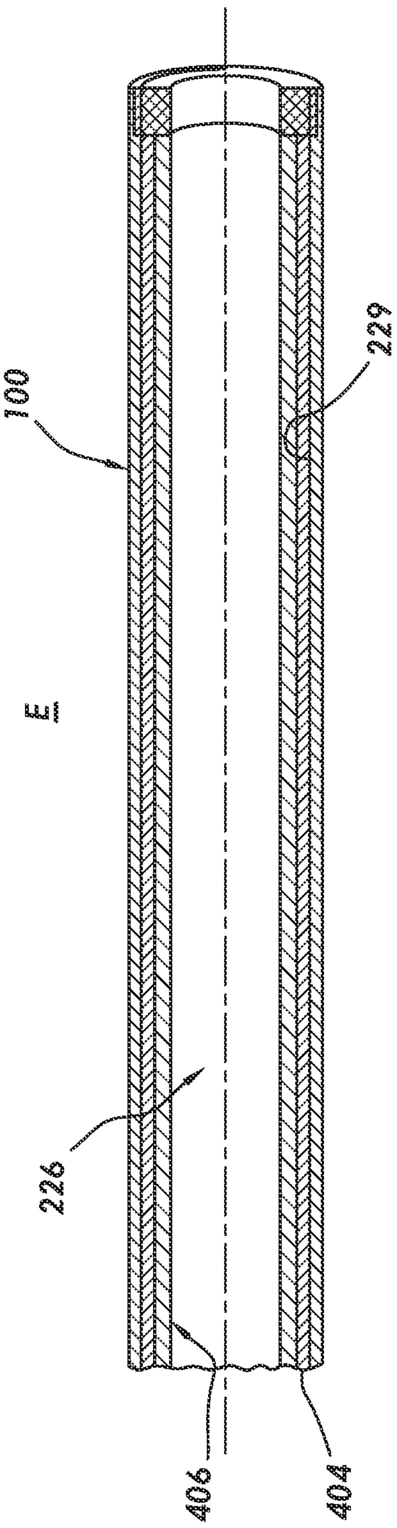
FIG. 3 is a cross-sectional side view of the portion of FIG. 2 showing a coating according to certain embodiments.

A portion of the formation testing tool 100 is shown in FIGS. 2 and 3. FIG. 2 is a perspective view of an example of a housing, apparatus, or tool 100 and first closure 204*a* and second closure 204*b*. The closures 204*a*/204*b* can include closure elements, such as valves, gaskets, end caps, or any other sealing device of suitable shape and size to seal the interior region or volume of the tool 100 from the external environment outside the tool. The tool 100 is shown in FIG. 3 after a coating has been applied. The tool can include a cylindrical housing having an interior surface 229. A base layer 404 can be deposited onto the interior surface 229 during the coating process to improve bonding with another coating layer 406 deposited onto layer 404. The tool can be sealed to create a containment area 226 for receiving the proxy gas.

An embodiment of the present disclosure is a system comprising a wellbore equipment; a coating applied to a portion of the wellbore equipment; a corrosive fluid; an initial concentration of a proxy fluid contained for a period of time within a containment area of the wellbore equipment adjacent to the coating; and a measuring device that determines a final concentration of the proxy fluid after the period of time has elapsed. Optionally, the wellbore equipment is a downhole formation tester tool, a measurement while drilling tool, or the inside or outside of a casing string or tubing string. Optionally, the corrosive fluid is selected from the group consisting of hydrogen sulfide, mercury, an acid, or combinations thereof. Optionally, the proxy fluid has similar chemical or physical properties to that of the corrosive fluid. Optionally, the similar chemical or physical properties are selected from the group consisting of molecular weight, vapor pressure, boiling point, electronegativity, ionizable protons, pKa, temperature desorption characteristics, and combinations thereof. Optionally, the proxy fluid is selected from water vapor, nitrous acid, sulfur dioxide, phosphoric acid, acetic acid, phenolic acid, or sulfoxylic acid. Optionally, the initial concentration of the proxy fluid is in a range of 50 to 500 parts per million. Optionally, the period of time is in a range of 1 to 100 hours. Optionally, the initial concentration of the proxy fluid is contained within the containment area at a testing temperature, a testing pressure, or a testing temperature and pressure. Optionally, a percent change between the final concentration and the initial concentration determines an effectiveness of the coating.

Another embodiment of the present disclosure is a method for testing an effectiveness of a coating applied to wellbore equipment comprising creating a containment area within the wellbore equipment containing the coating; introducing an initial concentration of a proxy fluid within the containment area; allowing the proxy fluid to remain within the containment area for a period of time; and measuring a final concentration of the proxy fluid after the period of time has elapsed. Optionally, the proxy fluid has similar chemical or physical properties to that of a corrosive fluid. Optionally, the similar chemical or physical properties are selected from the group consisting of molecular weight, vapor pressure, boiling point, electronegativity, ionizable protons, pKa, temperature desorption characteristics, and combinations thereof. Optionally, the corrosive fluid is selected from the group consisting of hydrogen sulfide, mercury, an acid, or combinations thereof. Optionally, the method further comprises calculating a percent change between the initial concentration and the final concentration of the proxy fluid. Optionally, the percent change determines the effectiveness of the coating. Optionally, an acceptable percent change is in a range of 75% to 100%. Optionally, the method further comprises determining an absorbance correlation between a corrosive fluid and the proxy fluid. Optionally, the method further comprises performing a second test of the effectiveness of the coating applied to the wellbore equipment, wherein the second test comprises: introducing an initial concentration of a second proxy fluid within the containment area; allowing the second proxy fluid to remain within the containment area for a period of time; and measuring a final concentration of the second proxy fluid after the period of time has elapsed, wherein the proxy fluid simulates a first corrosive fluid, wherein the second proxy fluid simulates a second corrosive fluid, and wherein the proxy fluid is different from the second proxy fluid and the first corrosive fluid is different from the second corrosive fluid. Optionally, the method further comprises: introducing the wellbore equipment into a subterranean formation after measuring the final concentration of the proxy fluid; returning the wellbore equipment to the surface after introduction; and performing a verification test to the effectiveness of the coating after returning the wellbore equipment, wherein the verification test comprises: creating a containment area within the wellbore equipment containing the coating; introducing an initial concentration of the proxy fluid within the containment area; allowing the proxy fluid to remain within the containment area for a period of time; and measuring a final concentration of the proxy fluid after the period of time has elapsed.

Therefore, the various embodiments are well adapted to attain the ends and advantages mentioned as well as those that are inherent therein. The particular embodiments disclosed above are illustrative only, as the various embodiments may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention.

As used herein, the words "comprise," "have," "include," and all grammatical variations thereof are each intended to have an open, non-limiting meaning that does not exclude additional elements or steps. While compositions, systems, and methods are described in terms of "comprising." "containing." or "including" various components or steps, the compositions, systems, and methods also can "consist essentially of" or "consist of" the various components and steps. It should also be understood that, as used herein, "first," "second," and "third," are assigned arbitrarily and are merely intended to differentiate between two or more proxy fluids, tests, etc., as the case may be, and does not indicate any sequence. Furthermore, it is to be understood that the mere use of the word "first" does not require that there be any "second," and the mere use of the word "second" does not require that there be any "third," etc.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent(s) or other documents that may be incorporated herein by reference, the definitions that are consistent with this specification should be adopted.

What is claimed is:

1. A system comprising:
- a wellbore equipment;
- a coating applied to a portion of the wellbore equipment;
- an initial concentration of a proxy fluid that has similar chemical or physical properties to that of a corrosive fluid contained for a period of time within a containment area of the wellbore equipment adjacent to the coating; and
- a measuring device that determines a final concentration of the proxy fluid after the period of time has elapsed.

2. The system according to claim 1, wherein the wellbore equipment is a downhole formation tester tool, a measurement while drilling tool, or the inside or outside of a casing string or tubing string.

3. The system according to claim 1, wherein the corrosive fluid is selected from the group consisting of hydrogen sulfide, mercury, an acid, or combinations thereof.

4. The system according to claim 1, wherein the similar chemical or physical properties are selected from the group consisting of molecular weight, vapor pressure, boiling point, electronegativity, ionizable protons, pKa, temperature desorption characteristics, and combinations thereof.

5. The system according to claim 1, wherein the proxy fluid is selected from water vapor, nitrous acid, sulfur dioxide, phosphoric acid, acetic acid, phenolic acid, or sulfoxylic acid.

6. The system according to claim 1, wherein the initial concentration of the proxy fluid is in a range of 50 to 500 parts per million.

7. The system according to claim 1, wherein the period of time is in a range of 1 to 100 hours.

8. The system according to claim 1, wherein the initial concentration of the proxy fluid is contained within the containment area at a testing temperature, a testing pressure, or a testing temperature and pressure.

9. The system according to claim 1, wherein a percent change between the final concentration and the initial concentration determines an effectiveness of the coating.

10. The system according to claim 9, wherein an acceptable percent change is in a range of 75% to 100%.

11. A method for testing an effectiveness of a coating applied to wellbore equipment comprising:
- creating a containment area within the wellbore equipment containing the coating;
- introducing an initial concentration of a proxy fluid within the containment area;
- allowing the proxy fluid to remain within the containment area for a period of time; and
- measuring a final concentration of the proxy fluid after the period of time has elapsed.

12. The method according to claim 11, wherein the proxy fluid has similar chemical or physical properties to that of a corrosive fluid.

13. The method according to claim 12, wherein the similar chemical or physical properties are selected from the group consisting of molecular weight, vapor pressure, boiling point, electronegativity, ionizable protons, pKa, temperature desorption characteristics, and combinations thereof.

14. The method according to claim 12, wherein the corrosive fluid is selected from the group consisting of hydrogen sulfide, mercury, an acid, or combinations thereof.

15. The method according to claim 11, further comprising calculating a percent change between the initial concentration and the final concentration of the proxy fluid.

16. The method according to claim 15, wherein the percent change determines the effectiveness of the coating.

17. The method according to claim 15, wherein an acceptable percent change is in a range of 75% to 100%.

18. The method according to claim 11, further comprising determining an absorbance correlation between a corrosive fluid and the proxy fluid.

19. The method according to claim 11, further comprising performing a second test of the effectiveness of the coating applied to the wellbore equipment, wherein the second test comprises:
- introducing an initial concentration of a second proxy fluid within the containment area;

allowing the second proxy fluid to remain within the containment area for a period of time; and measuring a final concentration of the second proxy fluid after the period of time has elapsed, wherein the proxy fluid simulates a first corrosive fluid, wherein the second proxy fluid simulates a second corrosive fluid, and wherein the proxy fluid is different from the second proxy fluid and the first corrosive fluid is different from the second corrosive fluid.

20. The method according to claim 11, further comprising:

introducing the wellbore equipment into a subterranean formation after measuring the final concentration of the proxy fluid;

returning the wellbore equipment to the surface after introduction; and performing a verification test to the effectiveness of the coating after returning the wellbore equipment, wherein the verification test comprises:

creating a containment area within the wellbore equipment containing the coating;

introducing an initial concentration of the proxy fluid within the containment area;

allowing the proxy fluid to remain within the containment area for a period of time; and measuring a final concentration of the proxy fluid after the period of time has elapsed.

* * * * *